United States Patent [19]

Shively

[11] Patent Number: 5,283,249
[45] Date of Patent: Feb. 1, 1994

[54] ANTICOCCIDIAL COMBINATIONS COMPRISING NICARBAZIN AND SEMDURAMICIN

[75] Inventor: Jesse E. Shively, Terre Haute, Ind.

[73] Assignee: Pfizer Inc., New York, N.Y.

[21] Appl. No.: 986,178

[22] Filed: Dec. 7, 1992

[51] Int. Cl.$^5$ .................. A01N 43/16; A01N 43/54
[52] U.S. Cl. ........................ 514/274; 514/460
[58] Field of Search ................... 514/274, 460

[56] References Cited

U.S. PATENT DOCUMENTS

| 4,218,438 | 12/1983 | Callender et al. | 424/251 |
| 4,218,438 | 8/1980 | Callender et al. | 424/115 |
| 4,804,680 | 2/1989 | Goudie et al. | 514/460 |

FOREIGN PATENT DOCUMENTS 0182117 10/1985 European Pat. Off. .

OTHER PUBLICATIONS

Cuckler, A. E. et al., Science, vol. 122, Aug. 1955, pp. 244–245.
Johnson, Joyce, et al. Exp. Parasitology 28:30–36 (1970).

*Primary Examiner*—Allen J. Robinson
*Attorney, Agent, or Firm*—Peter C. Richardson; Gregg C. Benson; Mervin E. Brokke

[57] ABSTRACT

Coccidioidal agents which contain the polyether antibiotic semduramicin and nicarbazin show synergistic effects in poultry.

4 Claims, No Drawings

ANTICOCCIDIAL COMBINATIONS COMPRISING NICARBAZIN AND SEMDURAMICIN

BACKGROUND OF THE INVENTION

The present invention relates to compositions of subtherapeutic doses of semduramicin, a polyether antibiotic and coccidiostat in combination with nicarbazin, an anticoccidial agent. These synergistic compositions control and/or prevent coccidiosis in poultry, particularly, strains of coccidia that are resistant to polyethers used alone.

Combinations of polyether antibiotics with nicarbazin are reported to be effective for control of coccidiosis-causing strains of Eimeria in U.S. Pat. No. 4,218,438. From among the combinations claimed in U.S. Pat. No. 4,218,438, the combination of narasin:nicarbazin at doses from 30:30 ppm up to 50:50 ppm was selected for development and is now in commercial use under the trade name Maxiban ®. The synergistic combination of the polyether antibiotic maduramicin and nicarbazin for use against coccidiosis in poultry is reported in EPO 182117. The combination of semduramicin with nicarbazin has not been previously reported.

SUMMARY OF THE INVENTION

The present invention provides a method for the control or prevention of coccidiosis in poultry which comprises administering to said poultry a subtherapeutic amount of semduramicin in combination with nicarbazin in amounts which, in combination, are synergistic in the control of at least one coccidiosis-causing strain of Eimeria, including strains that are resistant to ionophores used alone at their preferred dose.

In another aspect this invention provides a composition for the control of coccidiosis in poultry comprising a subtherapeutic amount of semduramicin and a subtherapeutic amount of nicarbazin. In yet another aspect this invention provides a poultry feedstuff comprising a first component which is semduramicin and a second component which is nicarbazin, said components being present in amounts which, in combination, are synergistic to at least one coccidiosis-causing strain of Eimeria.

DETAILED DESCRIPTION OF THE INVENTION

Nicarbazin is a complex of 4,4'-dinitrocarbanilide and 2-hydroxy-4,6-dimethylpyrimidine. See U.S. Pat. No. 2,731,382 and Science 122, 244 (1955).

Semduramicin is described in U.S. Pat. No. 4,804,680.

The methods and compositions of the present invention can be used with all species of poultry. Because of their economic importance, chickens and turkeys are the principal species requiring anticoccidial treatment. However, the present invention can be practiced with other poultry, such as ducks, geese, pheasants, and quail.

The present invention is practiced in the usual manner of anticoccidials. Since coccidiosis affects the intestinal tract, the compositions of the present invention are those which are suited for oral administration. Semduramicin is generally of low solubility in water, even in the sodium or other salt form. Therefore, the present invention is preferably practiced by administering the subject combinations in a feedstuff rather than in drinking water. Furthermore, it is the practice of the industry to supply poultry with only one source of feed, constituting the entire food supply of the poultry. Therefore, in a preferred practice of the present invention, the anticoccidial combinations are supplied in a total feed, with concentrations adjusted accordingly. Those skilled in the art, however, will recognize that concentrations are to be adjusted upward, should it be desired to supply poultry with multiple sources of food only one of which contains the combinations of the present invention.

The components of the present combinations are employed in amounts which, in combination, are synergistic as to at least one coccidiosis-causing organism. In general, the maxima to be employed in accordance with the present invention are the same as the maxima for anticoccidial treatment by the individual components. The lower limits in accordance with the present invention are generally less than for therapy or prophylaxis by the individual components, especially where the components are being used to minimize side effects of either individual component. Accordingly, the present invention is generally practiced with compositions containing from 5 to 25 ppm semduramicin combined with 20 to 125 ppm nicarbazin in a medicated feed. Preferred compositions are 10 to 25 ppm semduramicin and 30 to 50 ppm nicarbazin in medicated feed.

The compositions useful in the present invention may contain both components at subefficacious doses. By subefficacious is meant a dose which is less than that normally required for therapy or prophylaxis when the component is used alone. The combination dose according to the invention is, of course, efficacious. For instance, semduramicin is usually orally administered to poultry at doses of about 25 ppm. However, in the present feedstuff compositions, doses as low as 10 ppm are useful in controlling coccidiosis in poultry.

Likewise, nicarbazin's usual dose level, when orally administered in feedstuff compositions to poultry, is 125 ppm. Animal feedstuff compositions of the present invention contain nicarbazin at levels of 20 to 125 ppm preferably 30 to 50 ppm.

These levels of semduramicin and nicarbazin demonstrate significant control of coccidiosis caused by strains of Eimeria, as evidenced by increased survival of chickens and decreased lesion scores. The composition is useful in controlling lesions and mortality caused by strains of Eimeria that are resistant to ionophores when used alone at their preferred doses, in addition to strains that are sensitive to both ionophores and nicarbazin. Further, no adverse effects on weight gain are observed in the treated birds. The compositions of this invention were found to be superior to Maxiban ® in controlling resistant organisms. In addition, the compositions of this invention are safe for turkeys while Maxiban ® is not.

Animal feedstuff compositions containing the therapeutic and/or prophylactic levels of semduramicin and nicarbazin may be readily prepared by admixing these drugs with the feedstuff directly or by admixing a premix containing one or both of the drugs with the desired feedstuff.

Poultry feedstuffs of all types and formulae normally used in the poultry industry are appropriate for use in the present invention. The following provide examples of such formulae.

| Ingredients | Weight Percent |
|---|---|
| BROILER STARTER | |

-continued

| Ingredients | Weight Percent |
|---|---|
| Corn, Yellow Ground | 50.0 |
| Soybean Oil Meal, Solvent Extracted, Dehulled (50%) | 30.9 |
| Animal Fat | 6.5 |
| Fish Meal with Solubles (60%) | 5.0 |
| Corn Distillers Dried Solubles | 4.0 |
| Dicalcium Phosphate, Feed Grade | 1.8 |
| Calcium Carbonate (Ground Limestone) | 0.8 |
| Vitamin Premix TK-01 (1.03) | 0.5 |
| Salt (NaCl) | 0.3 |
| Trace Mineral Premix TK-01 (1.02) | 0.1 |
| Methionine Hydroxy Analog | 0.1 |
| TOTAL | 100.0 |

BROILER GROWER

| Ingredients | Weight Percent |
|---|---|
| Corn, Yellow Ground | 57.7 |
| Soybean Meal, Solvent Extracted, Dehulled (50%) | 31.7 |
| Animal Fat (Beef tallow) | 6.0 |
| Dicalcium Phosphate, Feed Grade | 2.7 |
| Calcium Carbonate (Ground Limestone) | 0.9 |
| Vitamin Premix TK-01 (1.03) | 0.5 |
| Salt (NaCl) | 0.2 |
| Methionine Hydroxy Analog | 0.2 |
| Trace Mineral Premix TK-01 (1.02) | 0.1 |
| TOTAL | 100.0 |

CHICK STARTER, LIGHT BREEDS

| Ingredients | Weight Percent |
|---|---|
| Corn, Yellow Ground | 56.3 |
| Soybean Meal, Solvent Extracted, Dehulled (50%) | 17.9 |
| Wheat Middlings | 10.0 |
| Corn Distillers Dried Solubles | 5.0 |
| Fish Meal with Solubles | 5.0 |
| Alfalfa Meal, Dehydrated (17%) | 2.5 |
| Dicalcium Phosphate, Feed Grade | 1.3 |
| Calcium Carbonate | 0.9 |
| Vitamin Premix | 0.5 |
| Salt (NaCl) | 0.3 |
| Methionine Hydroxy Analog | 0.2 |
| Trace Mineral Premix | 0.1 |
| TOTAL | 100.0 |

PULLET GROWER

| Ingredients | Weight Percent |
|---|---|
| Corn, Yellow Ground | 73.5 |
| Soybean Meal, Solvent Extracted, Dehulled (50%) | 21.9 |
| Dicalcium Phosphate, Feed Grade | 2.5 |
| Calcium Carbonate | 1.0 |
| Vitamin Premix | 0.5 |
| Salt (NaCl) | 0.3 |
| Methionine Hydroxy Analog | 0.2 |
| Trace Mineral Premix | 0.1 |
| TOTAL | 100.0 |

PULLET DEVELOPER

| Ingredients | Weight Percent |
|---|---|
| Corn, Yellow Ground | 67.5 |
| Oats, Ground Whole | 15.0 |
| Soybean Meal, Solvent Extracted, Dehulled (50%) | 13.4 |
| Dicalcium Phosphate, Feed Grade | 2.1 |
| Calcium Carbonate | 0.5 |
| Vitamin Premix | 0.5 |
| Methionine Hydroxy Analog | 0.3 |
| Salt (NaCl) | 0.2 |
| Trace Mineral Premix | 0.1 |
| TOTAL | 100.1 |

TURKEY STARTER

| Ingredients | Weight Percent |
|---|---|
| Soybean Meal, Solvent Extracted, Dehulled | 40.7 |
| Corn, Yellow, Ground | 39.7 |
| Fish Meal with Solubles | 5.0 |
| Beef Tallow | 5.0 |
| Corn Distillers Dried Solubles | 2.5 |
| Alfalfa Meal, Dehydrated (17%) | 2.5 |
| Dicalcium Phosphate, Feed Grade | 2.5 |
| Calcium Carbonate | 1.2 |
| Vitamin Premix | 0.5 |
| Salt (NaCl) | 0.2 |
| Trace Mineral Premix | 0.1 |
| Methionine Hydroxy Analog | 0.1 |
| TOTAL | 100.0 |

TURKEY FINISHER

| Ingredients | Weight Percent |
|---|---|
| Corn, Yellow, Ground | 71.2 |
| Soybean Meal, Solvent Extracted Dehulled (50%) | 9.9 |
| Corn Distillers Dried Solubles | 5.0 |
| Alfalfa Meal, Dehydrated (17%) | 5.0 |
| Animal Fat | 3.0 |
| Fish Meal with Solubles | 2.5 |
| Dicalcium Phosphate, Feed Grade | 1.7 |
| Calcium Carbonate | 0.5 |
| Vitamin Premix | 0.5 |
| Salt (NaCl) | 0.4 |
| Methionine Hydroxy Analog | 0.2 |
| Trace Mineral Premix | 0.1 |
| TOTAL | 100.0 |

The anticoccidial activity of compositions of the present invention are illustrated by the following non-limiting examples.

EXAMPLE 1

Maintaining Eimeria cultures

Recently propagated cultures of *Eimeria tenella* were used in trials to evaluate combinations of semduramicin and nicarbazin.

Propagation

Mature Hubbard Peterson broiler chicks were infected by oral administration of a suspension of $2 \times 10^5$ sporulated oocysts into the crop. Oocysts were collected from the ceca after 6 days.

Cecal contents and cecal scrapings were homogenized in a blender with dichromate and aerated in flasks in an incubator-shaker at 29° C. for 3 days. The cultures were centrifuged and resuspended in fresh dichromate and counted. Before use, the calculated numbers of oocysts were removed, centrifuged, washed with water and diluted to the correct volume.

Preparing Medicated Feed

The feed was a nonmedicated 18% to 22% protein ration. Drugs provided in a premix formula were blended with feed for at least 5 minutes in a cross flow shell blender. The feed was placed in the feeders the day before the test started. Water was also ready before the birds were received.

Setting up the Trial

In some trials, ten day old Hy-Line White leghorn chicks purchased as day old chicks from a commercial hatchery were maintained on 22% protein feed prior to random allotment to the test cages. Four cages were on unmedicated 18% protein feed, one pair as uninfected and one pair as infected controls. Five birds were placed by random selection in each cage and fed their respective test diets. The cages had ambient heating and lighting. Twenty four hours later the birds were infected. In other trials, 7-10 days old Hubbard Peterson broiler chickens were used, in which cases 3 cages of 10 birds per cage constituted a single treatment group. These received 22% protein diets during the growth and test period.

Infecting

The birds were weighed (by cage rather than individually) and given 0.5 to 1 ml inoculum into the crop via a repeating pipet. The inoculum consisted of $2 \times 10^5$ sporulated *E. tenella* oocysts.

Scoring

The birds were killed and scored on the seventh day (6 days PI). The birds from each cage were weighed, the abdominal cavity opened and the intestinal tract exposed. Pathology was determined after observations of the serosal and mucosal surfaces were made. Scoring was conducted by the method of Johnson & Reid (1970, Experimental Parasitology 28:30–36) as shown below with the exception that dead birds were not scored.

| *E. tenella* |
| --- |
| 0 = No gross lesions. |
| +1 = Very few scattered petechiae on the cecal wall; no thickening of the cecal walls; normal cecal content present. |
| +2 = Lesions more numerous with noticeable blood in the cecal contents; cecal wall is somewhat thickened; normal cecal contents present. |
| +3 = Large amounts of blood or cecal cores present; cecal walls greatly thickened; little, if any, fecal contents in the ceca. |
| +4 = Cecal wall greatly distended with blood or large caseous cores; fecal debris lacking or included in cores. |

EXAMPLE 2

A series of 30 trials was conducted using leghorn chicks and *E. tenalla* drug sensitive TES03 challenge strain versus semduramicin, nicarbazin and a combination treatment. Data from an across-trial summary of these studies are in Table 1. The combination of semduramicin at 10 ppm and nicarbazin at 30 ppm was highly effective for improving gains and reducing lesion scores and superior to the subefficacious levels of the individual drugs alone, e.g. semduramicin at 10 and nicarbazin at 30 ppm. The synergistic combination was as efficacious as semduramicin alone at 25 ppm or nicarbazin alone at 125 ppm.

EXAMPLE 3

A study was conducted in Hubbard Peterson broiler chickens infected with *E. tenella* ionophore resistant strain TER82 versus semduramicin, nicarbazin and a combination treatment. Results are summarized in Table 2. The combination of semduramicin at 20 ppm and nicarbazin at 40 ppm was highly effective for improving gains and reducing lesion scores from that of chicks receiving the subefficacious levels of individual drugs alone. The synergistic combination was as efficacious as nicarbazin alone at 125 ppm. As expected, semduramicin at 25 ppm showed little disease control as this challenge strain is resistant to ionophores alone.

EXAMPLE 4

A study was conducted in Hubbard Peterson broiler chickens infected with *E. tenella* ionophore resistant strain TER82 versus combinations of semduramicin and nicarbazin and Maxiban ®, the only polyether:nicarbazin combination of commerce (narasin:nicarbazin 1:1 combination). Results are summarized in Table 3. The combination of semduramicin at 20 ppm and nicarbazin at 40 ppm was as efficacious as nicarbazin alone at 125 ppm for improving gains and reducing lesion scores, and was unexpectedly substantially more effective than Maxiban ® in the range of doses used in commercial practice (30:30 ppm to 50:50 ppm). A combination containing 15 ppm of semduramicin and 30 ppm of nicarbazin was less effective than the 20:40 combination of semduramicin:nicarbazin, and a combination of 25:50 semduramicin:nicarbazin was no better than 20:40 semduramicin:nicarbazin. As expected, semduramicin at 25 ppm showed little disease control as this strain is resistant to ionophores alone.

TABLE 1

Lesion scores and weight gains for White Leghorn chickens infected with *E. tenella* ionophore sensitive strain TES03. Averages for 150 chickens per treatment (30 trials with 5 birds per treatment in each trial).

|  | Lesion Score | Weight Gain g/bird |
| --- | --- | --- |
| Uninfected Nonmedicated | 0.0 | 59.9 |
| Infected Nonmediated | 3.6 | 45.4 |
| Semduramicin 25 ppm | 1.6 | 56.5 |
| Semduramicin 10 ppm | 3.3 | 48.2 |
| Nicarbazin 125 ppm | 1.1 | 54.4 |
| Nicarbazin 30 ppm | 3.3 | 47.0 |
| Semduramicin 10 ppm + Nicarbazin 30 ppm | 1.2 | 58.2 |

TABLE 2

Lesion scores and weight gains for Hubbard Peterson broiler chickens infected with *E. tenella* ionophore resistant strain TER82. Averages for 30 chickens per treatment in a single trial.

|  | Lesion Score | Weight Gain g/bird |
| --- | --- | --- |
| Uninfected Nonmedicated | 0.0 | 236.2 |
| Infected Nonmediated | 2.6 | 215.2 |
| Semduramicin 25 ppm | 2.1 | 218.4 |
| Semduramicin 20 ppm | 2.1 | 224.4 |
| Nicarbazin 125 ppm | 0.5 | 208.5 |
| Nicarbazin 40 ppm | 2.0 | 210.3 |
| Semduramicin 20 ppm + Nicarbazin 40 ppm | 0.5 | 223.7 |

TABLE 3

Lesion scores and weight gains for Hubbard Peterson broiler chickens infected with *E. tenella* ionophore resistant strain TER82. Averages for 30 chickens per treatment in a single trial.

|  | Lesion Score | Weight Gain g/bird |
| --- | --- | --- |
| Uninfected Nonmedicated | 0.0 | 222.7 |
| Infected Nonmediated | 3.0 | 173.3 |
| Semduramicin 25 ppm | 3.0 | 182.0 |
| Nicarbazin 125 ppm | 1.1 | 191.2 |
| Semduramicin 15 ppm + Nicarbazin 30 ppm | 1.9 | 202.9 |
| Semduramicin 20 ppm + Nicarbazin 40 ppm | 1.1 | 214.1 |
| Semduramicin 25 ppm + Nicarbazin 50 ppm | 1.0 | 194.7 |
| Maxiban (Narasin 30 ppm + Nicarbazin 30 ppm) | 3.2 | 161.7 |
| Maxiban (Narasin 50 ppm + Nicarbazin 50 ppm) | 2.4 | 197.7 |

I claim:

1. A method for controlling coccidiosis in poultry comprising administering to said poultry a synergistically effective mixture of semduramicin and nicarbazin at the concentration of 40 to 75 ppm of said mixture in a poultry feed stuff, said mixture containing semduramicin and nicarbazin in the ratio of one part semduramicin to 2 to 3 parts nicarbazin.

2. The method of claim 1 wherein the ratio of semduramicin to nicarbazin is one to three.

3. The method of claim 1 wherein the ratio of semduramicin to nicarbazin is one to two.

4. A composition for controlling coccidiosis in poultry comprising a synergistically effective mixture of semduramicin and nicarbazin in a poultry feed stuff wherein the ratio of semduramicin to nicarbazin is one part of semduramicin to two to three parts nicarbazin in said feed stuff.

* * * * *